United States Patent
Condeelis et al.

(10) Patent No.: US 11,169,154 B2
(45) Date of Patent: Nov. 9, 2021

(54) PHOSPHOCOFILIN: COFILIN CO-LOCALIZATION INTENSITY AS A PREDICTOR OF METASTATIC RECURRENCE

(71) Applicants: ALBERT EINSTEIN COLLGE OF MEDICINE, Bronx, NY (US); KING'S COLLEGE LONDON, London (GB)

(72) Inventors: John Condeelis, Bronx, NY (US); Tony Tsz-Cheong Ng, London (GB); Gregory Weitsman, London (GB)

(73) Assignees: ALBERT EINSTEIN COLLEGE OF MEDICINE, Bronx, NY (US); KING'S COLLEGE LONDON, London (GB)

( * ) Notice: Subject to any disclaimer, the term of this patent is extended or adjusted under 35 U.S.C. 154(b) by 477 days.

(21) Appl. No.: 16/043,525

(22) Filed: Jul. 24, 2018

(65) Prior Publication Data
US 2019/0011448 A1    Jan. 10, 2019

Related U.S. Application Data

(63) Continuation of application No. 14/238,253, filed as application No. PCT/US2012/050765 on Aug. 14, 2012, now abandoned.

(60) Provisional application No. 61/523,539, filed on Aug. 15, 2011.

(51) Int. Cl.
G01N 33/574    (2006.01)
C07K 16/28     (2006.01)

(52) U.S. Cl.
CPC ... *G01N 33/57415* (2013.01); *C07K 16/2896* (2013.01); *G01N 33/57496* (2013.01); *G01N 2440/14* (2013.01); *G01N 2800/56* (2013.01)

(58) Field of Classification Search
CPC ............ C07K 16/2803; C07K 2317/73; A61K 2039/505; A61P 35/00
See application file for complete search history.

(56) References Cited

U.S. PATENT DOCUMENTS 7,662,547 B2 * 2/2010 Wu .................... A61K 38/1709
                                                       435/4
2010/0173338 A1   7/2010 Kimberely et al.
2011/0236903 A1   9/2011 McCellland
2011/0257102 A1  10/2011 Sy

OTHER PUBLICATIONS

Yoshioka et al., PNAS, 100:7247-7252, 2003).*
Disis et al. J Clin Oncol, 27:4685-4692, 2009.*
The International Search Report dated Jan. 3, 2013 for PCT Application No. PCT/US2012/50765.
Rheenen et al., entitled "A common cofilin activity cycle in invasive tumor cells and inflammatory cells,," J. Cell Sci, 2009, vol. 122(Pt 3), p. 305-11.
Hirayama et al., entitled "Cofilin plays a critical role in IL-8-dependant chemotaxis of neutrophilic HL-60 cells through changes in phosphorylation," J Leukoc Biol. 2007, vol. 81(3), p. 720-8.
Rheenen et al., entitled "EGF-induced PIP2 hydrolysis releases and activates cofilin locally in carcinoma cells," J Cell Biol. 2007, vol. 179, p. 1247-1259.
Zhang et al., entitled "Regulation of cofilin phosphorylation and asymmetry in collective cell migration during morphogenesis," Development, Feb. 2011, vol. 138(3), p. 455-65.
Wang et al., entitled "The cofilin pathway in breast cancer invasion and metastasis," Nat Rev Cancer, 2007, vol. 7(6), p. 429-40.
Hudes, entitled mTOR as a Target for Therapy of Renal Cancer, Clin Adv Hermatol Oncol, 2007, vol. 5(10), p. 772-4.
Nowak et al., Eur J Histochem, 2010, 54:59-66.
The International Preliminary Report on Patentability, dated Feb. 18, 2014 for PCT Application No. PCT/US2012/50765.

* cited by examiner

*Primary Examiner* — Mark Halvorson
(74) *Attorney, Agent, or Firm* — Fox Rothschild LLP

(57) ABSTRACT

Methods and products are provided for determining if a subject having a tumor is at risk of metastasis of the tumor. Specifically, the methods comprise detecting phosphorylated cofilin, and both phosphorylated and non-phosphorylated cofilin; quantifying the phosphorylated cofilin, and the total of phosphorylated and nonphosphorylated cofilin; and determining if a subject having the tumor is likely to experience metastasis of the tumor, based on the ratio of the amount of detected phosphorylated cofilin:total amount of phosphorylated and non-phosphorylated cofilin detected. Further disclosed are the types of tumor metastases that can be determined using the methods provided.

13 Claims, 3 Drawing Sheets
Specification includes a Sequence Listing.

A.

B.

SEQUENCE LISTING

```
<160> NUMBER OF SEQ ID NOS: 1

<210> SEQ ID NO 1
<211> LENGTH: 166
<212> TYPE: PRT
<213> ORGANISM: HOMO SAPIENS

<400> SEQUENCE: 1

Met Ala Ser Gly Val Ala Val Ser Asp Gly Val Ile Lys Val Phe Asn
1               5                   10                  15

Asp Met Lys Val Arg Lys Ser Ser Thr Pro Glu Glu Val Lys Lys Arg
            20                  25                  30

Lys Lys Ala Val Leu Phe Cys Leu Ser Glu Asp Lys Lys Asn Ile Ile
        35                  40                  45

Leu Glu Glu Gly Lys Glu Ile Leu Val Gly Asp Val Gly Gln Thr Val
    50                  55                  60

Asp Asp Pro Tyr Ala Thr Phe Val Lys Met Leu Pro Asp Lys Asp Cys
65                  70                  75                  80

Arg Tyr Ala Leu Tyr Asp Ala Thr Tyr Glu Thr Lys Glu Ser Lys Lys
                85                  90                  95

Glu Asp Leu Val Phe Ile Phe Trp Ala Pro Glu Ser Ala Pro Leu Lys
            100                 105                 110

Ser Lys Met Ile Tyr Ala Ser Ser Lys Asp Ala Ile Lys Lys Lys Leu
        115                 120                 125

Thr Gly Ile Lys His Glu Leu Gln Ala Asn Cys Tyr Glu Glu Val Lys
    130                 135                 140

Asp Arg Cys Thr Leu Ala Glu Lys Leu Gly Gly Ser Ala Val Ile Ser
145                 150                 155                 160

Leu Glu Gly Lys Pro Leu
                165
```

PHOSPHOCOFILIN: COFILIN CO-LOCALIZATION INTENSITY AS A PREDICTOR OF METASTATIC RECURRENCE

CROSS-REFERENCE TO RELATED APPLICATIONS

This application claims benefit of U.S. Provisional Application No. 61/523,539, filed Aug. 15, 2011, the contents of which are hereby incorporated by reference.

STATEMENT OF GOVERNMENT SUPPORT

This invention was made with government support under grant numbers CA100324 and CA150344 by the National Institutes of Health. The government has certain rights in the invention.

SEQUENCE LISTING INCORPORATION

The ".txt" Sequence Listing filed by EFS, and which is entitled 96700_1862_ST25.txt, is 2 kilobytes in size and was created on Jun. 25, 2012, is hereby incorporated by reference.

BACKGROUND OF THE INVENTION

Throughout this application various publications are referred to by number, or by author and year, in parentheses. Full citations for these references may be found at the end of the specification. The disclosures of these publications are hereby incorporated by reference in their entirety into the subject application to more fully describe the art to which the subject invention pertains.

Virtually all cancers, including cancers of the blood and the lymphatic system, can form metastatic tumors. Although rare, the metastasis of blood and lymphatic system cancers to the lungs, heart, central nervous system, and other tissues has been reported. The most common sites of cancer metastasis are the lungs, bones, and liver. Although most cancers have the ability to spread to many different parts of the body, they usually spread to one site more often than others. Metastatic cancer may be treated with systemic therapy (chemotherapy, biological therapy, targeted therapy, hormonal therapy), local therapy (surgery, radiation therapy), or a combination of these treatments. However, identification of metastatic risk is still a difficult task.

Breast cancer is one of the most frequent malignant neoplasms occurring in women in developed countries and metastasis of breast cancer is the main cause of death in these patients. One out of three cancers diagnosed among US women is due to breast cancer; 212,920 new invasive breast cancer cases and an additional 61,980 in situ breast cancer cases are expected to be diagnosed in 2006. Around 40,970 women are expected to die from breast cancer in 2006 (American Cancer Society, Breast Cancer Facts and FIGS. 2006). The metastasis of 10-15% of patients with breast cancer is aggressive and can take between 3-10 years to be manifested after the initial diagnosis. Currently, the prognosis in 70% of patients cannot be accurately determined resulting in the unnecessary treatment of many patients who will not benefit and may be injured by radiation and chemotherapy.

The idea of personalized medicine and molecular profiling for prognostic tests has lead to a plethora of studies in the past 10 years in search of genetic determinants of metastasis. Such studies have identified gene sets, or "signatures", the expression of which in primary tumors is associated with higher risk of metastasis and poor disease outcome for the patients. Early methods of analysis treated the tumor as a whole, without respect to the different metastatic stages or the microenvironments. For example, the first molecular classification of tumors and identification of gene signatures associated with metastasis, were all derived from whole pieces of tumor tissue (1-6). These signatures were predictive of metastasis in patients and an important step towards applying these methods in clinical care. However, these signatures, mostly built to act as a general prognostic tool for the clinic, gave little information about the molecular biology of the different cell types comprising the tumor tissue and little insight into the specific mechanisms of metastasis.

It is now known that tumors are highly heterogeneous, that not all cells within a tumor are migratory and invasive, and that the tumor microenvironment gives spatial-temporal cues to tumor cells for invasion and metastasis. In addition, metastasis is a multi-step process that involves the escape of cells from the primary tumor either via lymphatic or blood vessels, transport to and arrest in a target organ, and growth of metastases in the target organ. Each of these steps is a multicomponent process, with potentially different tumor cell properties and molecules playing critical roles, and therefore each of these steps separately deserves detailed attention. More recent signatures give such emphasis in detailed analysis of the role of the microenvironment in metastasis (7), as well as analysis of the tissue tropism for metastatic growth (8). The latter studies have been informative in prognosis of site-specific metastasis, as well as the cell biology behind the mechanisms of extravasation, homing and colonization at the distant metastatic site (9-11).

The availability of a marker that uniquely and specifically identifies metastatic disease or potential therefor early in treatment will allow for accurate prediction of disease course and allow appropriate prophylactic or therapeutic treatment. The present invention addresses this need.

SUMMARY OF THE INVENTION

A method of determining if a subject having a tumor is likely to experience metastasis of the tumor comprising contacting a sample of the tumor with (a) a detectable agent that specifically binds phosphorylated cofilin and (b) a detectable agent which binds both phosphorylated cofilin and non-phosphorylated cofilin and quantifying (i) the phosphorylated cofilin bound by (a) and (ii) the total of phosphorylated cofilin and non-phosphorylated cofilin bound by (b), wherein a ratio of the amount of phosphorylated cofilin bound:total amount of phosphorylated cofilin and non-phosphorylated cofilin bound in excess of a predetermined ratio value indicates that the subject having the tumor is likely to experience metastasis of the tumor.

A method is provided of mitigating the risk of metastasis of a tumor in a subject comprising administering to a subject identified by any of the methods described hereinabove as likely to experience metastasis of the tumor an anti-metastatic therapy.

A kit is provided for determining if a subject having a tumor is likely to experience metastasis of the tumor, the kit comprising (a) a detectable agent that specifically binds phosphorylated cofilin and (b) a detectable agent which binds to phosphorylated cofilin and which binds to non-phosphorylated cofilin, and instructions for use.

A computer system is provided comprising a program for determining if a subject having a tumor is likely to experience metastasis of the tumor, the computer system comprising a processor and a memory encoding one or more programs coupled to the processor, wherein the one or more programs quantify phosphorylated cofilin stained with a detectable agent in a sample from the tumor in the subject and quantify total phosphorylated cofilin and un-phosphorylated cofilin stained with a different detectable agent in the sample and compare the ratio of the two quantities to a predetermined ratio value, and instructions for use.

This invention also provides a computer system comprising a program for determining if a subject having a tumor is likely to experience metastasis of the tumor, the computer system comprising a processor and a memory encoding one or more programs coupled to the processor, wherein the processor effects the one or more programs to quantify phosphorylated cofilin stained with a detectable agent in a sample from the tumor in the subject and quantify total phosphorylated cofilin and un-phosphorylated cofilin stained with a different detectable agent in the sample and determine the ratio thereof.

This invention also provides an apparatus comprising the computer system described herein, and instructions for use.

DETAILED DESCRIPTION OF THE INVENTION

Figure 1A:
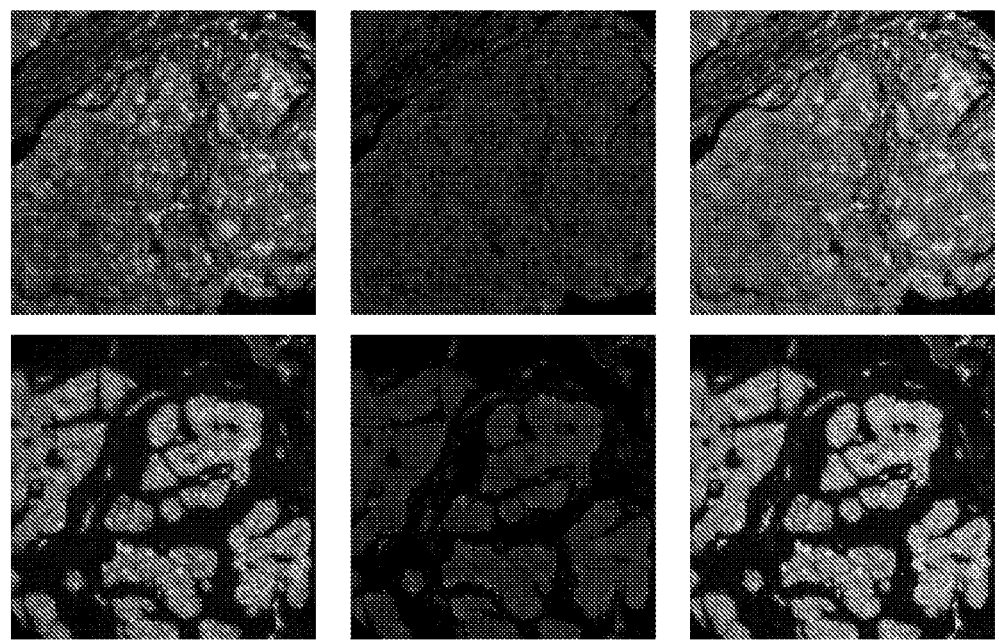
FIG. 1(A)-1(B). Phosphocofilin:total cofilin colocalization intensity: Univariate analysis of its influence on relapse/metastasis-free survival. 1(A) shows staining with Anti-pCofilin IgG-Cy2 (left hand two panels) and Anti-pan Cofilin IgG-Cy3 (middle two panels). The images are merged in the right hand two panels. Representative images of infiltrating ductal carcinoma stained with anti-phospho-Ser-3-cofilin and anti-pan-cofilin antibodies. Co-localization analysis was performed on 69 patients (30 patients from a 1980's cohort and 39 patients from a 1990's cohort). A significant increase in the risk of recurrence due to distal metastasis was observed with higher levels of phosphorylated cofilin being present in the tumours.

A method of determining if a subject having a tumor is likely to experience metastasis of the tumor comprising contacting a sample of the tumor with (a) a detectable agent that binds phosphorylated cofilin and (b) a detectable agent which binds both phosphorylated cofilin and non-phosphorylated cofilin and quantifying (i) the phosphorylated cofilin bound by (a) and (ii) the total of phosphorylated cofilin and non-phosphorylated cofilin bound by (b), wherein a ratio of the amount of phosphorylated cofilin bound:total amount of phosphorylated cofilin and non-phosphorylated cofilin bound in excess of a predetermined ratio value, or a colocalization intensity value (IF) within the highly colocalized areas marked by (a) and (b) in excess of a predetermined IF value, indicates that the subject having the tumor is likely to experience metastasis of the tumor.

In an embodiment, the tumor is a breast cancer tumor, or a tumor of the nasopharynx, pharynx, lung, bone, brain, sialaden, stomach, esophagus, testes, ovary, uterus, liver, small intestine, appendix, colon, rectum, gall bladder, pancreas, kidney, urinary bladder, breast, cervix, vagina, vulva, prostate, thyroid or skin.

In an embodiment, IF is intensity of (a) in pixels of an image of the sample×intensity of (b) in pixels of the image of the sample, optionally first masking out pixels with low Pearson distribution. In an embodiment, one of agent (a) or (b) comprises Cy2 and the other agent comprises Cy3, and IF=$I_{Cy2} \times I_{Cy3}$, where $I_{Cy2}$ is the intensity of Cy2 and $I_{Cy3}$ is the intensity of Cy3.

In an embodiment, the tumor is a tumor of the nasopharynx, pharynx, lung, bone, brain, sialaden, stomach, esophagus, testes, ovary, uterus, liver, small intestine, appendix, colon, rectum, gall bladder, pancreas, kidney, urinary bladder, breast, cervix, vagina, vulva, prostate, thyroid or skin.

In an embodiment, the tumor is a solid tumor.

In an embodiment, the sample is a biopsy sample.

In an embodiment, the sample is surgically removed from the subject.

In an embodiment, the detectable agent that binds phosphorylated cofilin comprises an antibody that binds phosphorylated cofilin. In an embodiment, the detectable agent specifically binds phosphorylated cofilin In an embodiment, the detectable agent specifically binds non-phosphorylated cofilin. In an embodiment, the detectable agent that specifically binds phosphorylated cofilin comprises an antibody or antigen-binding fragment thereof. In an embodiment, the detectable agent that specifically binds non-phosphorylated cofilin comprises an antibody or antigen-binding fragment thereof.

In an embodiment, the detectable agent which binds to phosphorylated cofilin and to non-phosphorylated cofilin comprises an antibody which binds phosphorylated cofilin and which also binds non-phosphorylated cofilin.

In an embodiment, the detectable agent which binds to phosphorylated cofilin and to non-phosphorylated cofilin and/or the detectable agent which binds to phosphorylated cofilin comprises a fluorescent marker.

In an embodiment, the detectable agent that binds to phosphocofilin comprises a different fluorescent dye than the detectable agent that binds to phosphorylated cofilin and to non-phosphorylated cofilin.

In an embodiment the method further comprises obtaining the sample of the tumor. In an embodiment, the sample is obtained from the subject.

In an embodiment, the method comprises imaging the stained sample, for example fluorescently stained by the detectable agents comprising fluorescent moieties. In an embodiment, the pixels of the images obtained with low overlap distribution (ri<1.0) are excluded from the analysis. In an embodiment, the pixels of the images obtained with low Pearson distribution (pi<1.0) are excluded from the analysis. In an embodiment, the colocalization (of the non-phosphorylated cofilin detectable agent and the phosphorylated cofilin detectable agent) is determined by intensity analysis. In an embodiment, the colocalization is determined for one or more cells of the sample.

In an embodiment, the colocalization of phosphorylated cofilin and non-phosphorylated cofilin is used as the determinant of whether the tumor is likely to metastasize. In an embodiment, an IF in excess of the predetermined control value indicates the tumor is likely to metastasize. For example, determination of IF within the highly colocalized areas between detectable agent for phosphorylated cofilin comprising Cy2 and a pan-cofilin detectable agent comprising Cy3 (first defined by masking out the pixels with low Pearson distribution) is employed; IF=Icy2×Icy3.

In an embodiment of the inventions described herein, the phosphorylated cofilin and non-phosphorylated cofilin are human cofilin. In an embodiment, the phosphorylated cofilin and non-phosphorylated cofilin are human cofilin 1.

In an embodiment of the inventions described herein, the cofilin comprises SEQ ID NO:1.

In an embodiment of the inventions described herein, the sample is a paraffin-embedded biopsy sample.

In an embodiment of the inventions described herein, the detectable agent which binds to phosphorylated cofilin and which binds to non-phosphorylated cofilin comprises an anti-pan-cofilin antibody.

In an embodiment of the inventions described herein, the detectable agent which specifically binds to phosphorylated cofilin comprises an anti-phospho-Ser-3-cofilin antibody. In an embodiment, the detectable agent which specifically binds to phosphorylated cofilin comprises an anti-pCofilin IgG-Cy2 antibody. In an embodiment, the detectable agent which specifically binds to phosphorylated cofilin and binds to non-phosphorylated cofilin comprises anti-pan cofilin IgG-Cy3 antibody.

In an embodiment of the inventions described herein, the predetermined ratio value is determined from one or more subjects with malignant tumors which have not metastasized.

In an embodiment of the inventions described herein, the predetermined ratio value is determined from one or more subjects who have had a malignant tumor for at least five years which malignant tumor has not metastasized.

In an embodiment of the methods described herein, the method further comprises administering to the subject found likely to experience metastasis of the tumor an anti-metastatic therapy.

A method is provided of mitigating the risk of metastasis of a tumor in a subject comprising administering to a subject identified by any of the methods described hereinabove as likely to experience metastasis of the tumor, an anti-metastatic therapy.

A kit is provided for determining if a subject having a tumor is likely to experience metastasis of the tumor, the kit comprising (a) a detectable agent that specifically binds phosphorylated cofilin and (b) a detectable agent which binds to phosphorylated cofilin and which binds to non-phosphorylated cofilin, and instructions for use. In an embodiment, the subject is naïve to cytotoxic and/or chemotherapeutic treatment. In an embodiment, the subject has been subjected to a cytotoxic and/or chemotherapeutic treatment. In an embodiment, the subject has been subjected to a cytotoxic and/or chemotherapeutic treatment of the tumor. The method can assess the metastatic potential of an individual's tumor post cytotoxic chemotherapy to metastasize.

A computer system is provided comprising a program for determining if a subject having a tumor is likely to experience metastasis of the tumor, the computer system comprising a processor and a memory encoding one or more programs coupled to the processor, wherein the one or more programs quantify phosphorylated cofilin stained with a detectable agent in a sample from the tumor in the subject and quantify total phosphorylated cofilin and un-phosphorylated cofilin stained with a different detectable agent in the sample and compare the ratio of the two quantities to a predetermined ratio value, and instructions for use.

This invention also provides a computer system comprising a program for determining if a subject having a tumor is likely to experience metastasis of the tumor, the computer system comprising a processor and a memory encoding one or more programs coupled to the processor, wherein the processor effects the one or more programs to quantify phosphorylated cofilin stained with a detectable agent in a sample from the tumor in the subject and quantify total phosphorylated cofilin and un-phosphorylated cofilin stained with a different detectable agent in the sample and determine the ratio thereof.

In an embodiment, the processor effects the program to compare the ratio determined of the amount of phosphorylated cofilin bound:total amount of phosphorylated cofilin and non-phosphorylated cofilin bound to the predetermined ratio value. In an embodiment, a ratio of the amount of phosphorylated cofilin bound:total amount of phosphorylated cofilin and non-phosphorylated cofilin bound in excess of a predetermined ratio value indicates that the subject having the tumor is likely to experience metastasis of the tumor.

This invention also provides an apparatus comprising the computer system described herein, and instructions for use. In an embodiment, the apparatus further comprises an imaging device. Imaging devices are known in the art, and include fluorescence imaging devices. In an embodiment, the apparatus further comprises a detectable agent that specifically binds phosphorylated cofilin and a detectable agent which binds to phosphorylated cofilin and which binds to non-phosphorylated cofilin. In an embodiment, the detectable agents are antibodies or antigen-binding fragments of antibodies.

In an embodiment of the kits, computer systems and apparatus described herein, the detectable agent which specifically binds to phosphorylated cofilin comprises an anti-phospho-Ser-3-cofilin antibody. In an embodiment, the detectable agent which specifically binds to phosphorylated cofilin comprises an anti-pCofilin IgG-Cy2 antibody. In an embodiment, the detectable agent which specifically binds to phosphorylated cofilin and binds to non-phosphorylated cofilin comprises anti-pan cofilin IgG-Cy3 antibody.

As used herein, being determined to "likely experience metastasis" of a tumor means that the subject is expected to have metastasis of the tumor within five years after being determined as "likely to" by performance of the method on the subject.

As used herein, not being determined to likely experience metastasis of a tumor means that the subject is not expected to have metastasis of the tumor within five years after being not being determined as likely to by performance of the method on the subject.

As used herein, a "sample" may comprise any clinically relevant tissue sample, such as a tumor biopsy, surgically removed sample or fine needle aspirate. The sample may be treated before performance of the method in order to aid in visualization of staining and/or preservation of the native cofilin phosphorylation/non-phosphorylation status in the tumor. The sample may be taken from a human subject, or, in a veterinary context, from non-human subjects such as ruminants, horses, swine or sheep, or from domestic companion animals such as felines and canines.

In an embodiment of the kit of the invention a control sample is provided, wherein the control sample is a standardized or normalized sample (e.g. derived from a normal population) which is, for example, free of cancer, or a standard human tissue reference which tissue corresponds to the tissue in which the tumor being sampled is, or from samples of tumors from patients (e.g. from a cohort study) who did not experience metastasis, e.g. did not experience metastasis of the tumor within 5 years of the sample being collected. The kit may comprise other elements, for example buffer, preservative etc.

In an embodiment, the kit or the apparatus further comprises a sample from the subject. In an embodiment, the kit or the apparatus does not comprise a sample from the subject.

The term "tumor," as used herein, refers to all neoplastic cell growth and proliferation, and all pre-cancerous and cancerous cells and tissues. In an embodiment the tumor is a breast cancer tumor.

As used herein, "metastasize" or grammatical equivalent thereof means, in regard to a cancer or tumor, to spread from one organ or tissue of a subject to another non-adjacent organ or non-adjacent tissue of the subject.

As used herein, an "anti-metastatic" therapy is any art-recognized therapy used to reduce the likelihood or incidence of metastasis in an individual. In non-limiting examples the anti-metastatic therapy is administration of trastuzumab and/or bevacizumab.

As used herein, an "anti-recurrent" therapy is any art-recognized therapy used to reduce the recurrence of a cancer or of a tumor type in an individual.

As used herein, "recurrence" of a tumor, means a later recurrence of the tumor in the same location in the individual, or a later recurrence of the same tumor type.

In an embodiment the cofilin (phosphorylated and non-phosphorylated) is human cofilin. In an embodiment the human cofilin comprises the following sequence (GenBank: CAA64685.1):

```
                                        (SEQ ID NO: 1)
MASGVAVSDG VIKVFNDMKV RKSSTPEEVK KRKKAVLFCL

SEDKKNIILE EGKEILVGDV GQTVDDPYAT FVKMLPDKDC

RYALYDATYE TKESKKEDLV FIFWAPESAP LKSKMIYASS

KDAIKKKLTG IKHELQANCY EEVKDRCTLA EKLGGSAVIS

LEGKPL
```

As used herein, "detectable" agents comprise, but are not limited to moieties such as fluorescent dyes, radionuclides, chemiluminescent agents, microparticles, nanoparticles, enzymes, colorimetric labels, magnetic labels, haptens, molecular beacons and aptamer beacons. Non-limiting examples include Cy2, Cy3, fluorochromes such as fluorescein isothiocyanate (FITC), Texas Red, phycoerythrin, allophycocyanin, 6-carboxyfluorescein (6-FAM), 2',7'-dimethoxy-4',5'-dichloro-6-carboxyfluorescein (JOE), 5-carboxyfluorescein (5-FAM) or N,N,N',N'-tetramethyl-6-carboxyrhodamine (TAMRA), radioactive labels, e.g. $^{32}$P, $^{35}$S, $^{3}$H; etc. Such detectable agents can also comprise antibodies, or antibody fragments, or other molecules, to which the moieties listed herein are bound, conjugated or otherwise attached. In an embodiment at least one of the detectable agents comprises a fluorescent dye. In an embodiment both of the detectable agents each comprise a fluorescent dye. In an embodiment at least one of the detectable agents comprises an antibody, or antibody fragment, having attached thereto a fluorescent dye. In an embodiment both of the detectable agents each comprise an antibody, or antibody fragment, each having attached thereto a fluorescent dye, but wherein the fluorescent dyes have different absorption and/or emission spectra. In an embodiment the detectable agent is an antibody or antigen-binding fragment thereof which is detectable by a labeled secondary antibody, e.g. having a fluorescent label. In an embodiment each of detectable agents (a) and (b) is a different antibody or antigen-binding fragment which is detectable by a different labeled secondary antibody, e.g. having a fluorescent label.

As used herein, the term "antibody" refers to an intact antibody, i.e. with complete Fc and Fv regions. "Fragment" refers to any portion of an antibody, or portions of an antibody linked together, such as a single-chain Fv (scFv), which is less than the whole antibody but which is an antigen-binding portion and which competes with the intact antibody of which it is a fragment for specific binding. As such a fragment can be prepared, for example, by cleaving an intact antibody or by recombinant means. See generally, Fundamental Immunology, Ch. 7 (Paul, W., ed., 2nd ed. Raven Press, N.Y. (1989), hereby incorporated by reference in its entirety). Antigen-binding fragments may be produced by recombinant DNA techniques or by enzymatic or chemical cleavage of intact antibodies or by molecular biology techniques. In some embodiments, a fragment is an Fab, Fab', F(ab')$_2$, F$_d$, F$_v$, complementarity determining region (CDR) fragment, single-chain antibody (scFv), (a variable domain light chain (V$_L$) and a variable domain heavy chain (V$_H$) linked via a peptide linker. In an embodiment the linker is 10-25 amino acids in length. In an embodiment the peptide linker comprises glycine, serine and/or threonine residues. For example, see Bird et al., Science, 242: 423-426 (1988) and Huston et al., Proc. Natl. Acad. Sci. USA, 85:5879-5883 (1988) each of which are hereby incorporated by reference in their entirety), or a polypeptide that contains at least a portion of an antibody that is sufficient to confer specific antigen binding on the polypeptide, including a diabody. From N-terminus to C-terminus, both the mature light and heavy chain variable domains comprise the regions FR1, CDR1, FR2, CDR2, FR3, CDR3 and FR4. The assignment of amino acids to each domain is in accordance with the definitions of Kabat, Sequences of Proteins of Immunological Interest (National Institutes of Health, Bethesda, Md. (1987 and 1991)), Chothia & Lesk, J. Mol. Biol. 196:901-917 (1987), or Chothia et al., Nature 342:878-883 (1989), each of which are hereby incorporated by reference in their entirety). As used herein, the term "polypeptide" encompasses native or artificial proteins, protein fragments and polypeptide analogs of a protein sequence. A polypeptide may be monomeric or polymeric. As used herein, an Fd fragment means an antibody fragment that consists of the V$_H$ and CH1 domains; an Fv fragment consists of the V$_l$ and V$_H$ domains of a single arm of an antibody; and a dAb fragment (Ward et al., Nature 341:544-546 (1989) hereby incorporated by reference in its entirety) consists of a V$_H$ domain.

In some embodiments, fragments are at least 5, 6, 8 or 10 amino acids long. In other embodiments, the fragments are at least 14, at least 20, at least 50, or at least 70, 80, 90, 100, 150 or 200 amino acids long.

In an embodiment, one or more detectable agents are monoclonal antibodies. The term "monoclonal antibody" is not intended to be limited as regards to the source of the antibody or the manner in which it is made (e.g., by hybridoma, phage selection, recombinant expression, transgenic animals, etc.). The term "monoclonal antibody" as used herein refers to an antibody member of a population of substantially homogeneous antibodies, i.e., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations, which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins.

A "human antibody" is one whose sequences correspond to (i.e. have the same in sequence as) an antibody produced by a human and/or has been made using any of the techniques for making human antibodies as disclosed herein. This definition of a human antibody specifically excludes a humanized antibody. A "human antibody" as used herein can be produced using various techniques known in the art, including phage-display libraries (e.g. Hoogenboom and Winter, J. Mol. Biol., 227:381 (1991); Marks et al., J. Mol. Biol., 222:581 (1991), hereby incorporated by reference in its entirety), by methods described in Cole et al., Monoclonal Antibodies and Cancer Therapy, Alan R. Liss, p. 77 (1985) (hereby incorporated by reference in its entirety); Boerner et al., J. Immunol., 147(1):86-95 (1991) (hereby incorporated by reference in its entirety), van Dijk and van de Winkel, Curr. Opin. Pharmacol., 5: 368-74 (2001) (hereby incorporated by reference in its entirety), and by administering the relevant antigen (e.g. phosphocofilin) to a transgenic animal that has been modified to produce such antibodies in response to antigenic challenge, but whose endogenous loci have been disabled, e.g., immunized xenomice (see, e.g., U.S. Pat. Nos. 5,939,598; 6,075,181; 6,114,598; 6,150,584 and 6,162,963 to Kucherlapati et al. regarding XENOMOUSE technology, each of which patents are hereby incorporated by reference in their entirety), e.g. VelocImmune® (Regeneron, Tarrytown, N.Y.), e.g. UltiMab® platform (Medarex, now Bristol Myers Squibb, Princeton, N.J.). See also, for example, Li et al., Proc. Natl. Acad. Sci. USA, 103:3557-3562 (2006) regarding human antibodies generated via a human B-cell hybridoma technology. See also KM Mouse® system, described in PCT Publication WO 02/43478 by Ishida et al., in which the mouse carries a human heavy chain transchromosome and a human light chain transgene, and the TC mouse system, described in Tomizuka et al. (2000) Proc. Natl. Acad. Sci. USA 97:722-727, in which the mouse carries both a human heavy chain transchromosome and a human light chain transchromosome, both of which are hereby incorporated by reference in their entirety. In each of these systems, the transgenes and/or transchromosomes carried by the mice comprise human immunoglobulin variable and constant region sequences.

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from a hypervariable region (HVR) of the recipient are replaced by residues from a HVR of a non-human species (donor antibody) such as mouse, rat, rabbit, or nonhuman primate having the desired specificity, affinity, and/or capacity. In some instances, FR residues of the human immunoglobulin variable domain are replaced by corresponding non-human residues. These modifications may be made to further refine antibody performance. Furthermore, in a specific embodiment, humanized antibodies may comprise residues that are not found in the recipient antibody or in the donor antibody. In an embodiment, the humanized antibodies do not comprise residues that are not found in the recipient antibody or in the donor antibody. In general, a humanized antibody will comprise substantially all of at least one, and typically two, variable domains, in which all or substantially all of the hypervariable loops correspond to those of a non-human immunoglobulin, and all or substantially all of the FRs are those of a human immunoglobulin sequence. The humanized antibody optionally will also comprise at least a portion of an immunoglobulin constant region (Fc), typically that of a human immunoglobulin. See, e.g., Jones et al., Nature 321:522-525 (1986); Riechmann et al., Nature 332:323-329 (1988); Presta, Curr. Op. Struct. Biol. 2:593-596 (1992); Vaswani and Hamilton, Ann. Allergy, Asthma & Immunol. 1:105-115 (1998); Harris, Biochem. Soc. Transactions 23:1035-1038 (1995); Hurle and Gross, Curr. Op. Biotech. 5:428-433 (1994); and U.S. Pat. Nos. 6,982,321 and 7,087,409, the contents of each of which references and patents are hereby incorporated by reference in their entirety. In one embodiment where the humanized antibodies do comprise residues that are not found in the recipient antibody or in the donor antibody, the Fc regions of the antibodies are modified as described in WO 99/58572, the content of which is hereby incorporated by reference in its entirety.

Techniques to humanize a monoclonal antibody are described in U.S. Pat. Nos. 4,816,567; 5,807,715; 5,866,692; 6,331,415; 5,530,101; 5,693,761; 5,693,762; 5,585,089; and 6,180,370, the content of each of which is hereby incorporated by reference in its entirety.

As used herein, the terms "specifically binds" or grammatical equivalent thereof refers to when an antibody binds to an antigen with a dissociation constant that is <1 µM, preferably <1 nM and most preferably <10 pM. For example, an antibody which specifically binds to phosphocofilin will bind to phosphocofilin but not to non-phosphorylated cofilin to any detectable extent or to other cellular components. In an embodiment a detectable agent which binds to phosphorylated cofilin and to non-phosphorylated cofilin does not bind to any detectable level to any other cellular component.

The "predetermined ratio value" or "predetermined colocalization intensity" referred to herein can readily be determined. It can be taken from a population group and determined empirically or assigned based on experimental data. In an embodiment, the predetermined ratio value is the ratio of the amount of phosphorylated cofilin to the total amount of phosphorylated cofilin and non-phosphorylated cofilin as determined form one or more tumor samples at which, and below which, distal metastasis is not likely to occur. This value can be a normalized value, can be determined for the particular population at hand, from a control group, and/or from cohort studies which provide metastasis incidence. In an embodiment, the predetermined colocalization intensity value (IF), within the highly colocalized areas between Cy2 and Cy3 (which in an embodiment is first defined by masking out the pixels with low Pearson distribution), is given by the product of the local fluorescence intensity in each channel: IF=Icy2×Icy3, as determined form one or more tumor samples at which, and below which, distal metastasis is not likely to occur. This value can be a normalized value, can be determined for the particular population at hand, from a control group, and/or from cohort studies which provide metastasis incidence.

Embodiments of the invention and all of the functional operations described in this specification, for example quantification of phosphocofilin:total cofilin ratio (or phosphocofilin:total cofilin colocalization intensity) and comparison thereof to a predetermined control ratio, can be implemented in digital electronic circuitry, or in computer software, firmware, or hardware, including the structures disclosed in this specification and their structural equivalents, or in combinations of one or more of them. Embodiments of the invention can be implemented as one or more computer program products, i.e., one or more modules of computer program instructions encoded on a computer readable medium for execution by, or to control the operation of, data processing apparatus. The computer readable medium can be a machine readable storage device, a machine readable storage substrate, a memory device, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The methods/processes and logic flows described in this specification can be performed by one or more programmable processors executing one or more computer programs to perform functions by operating on input data and generating output. The methods/processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device. Computer-readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, embodiments of the invention can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

Embodiments of the invention can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the invention, or any combination of one or more such back-end, middleware, or front-end components. The components of the system can be interconnected by any form or medium of digital data communication, e.g., a communication network. Examples of communication networks include a local area network ("LAN") and a wide area network ("WAN"), e.g., the Internet.

The computing system can include clients and servers. A client and server are generally remote from each other and typically interact through a communication network. The relationship of client and server arises by virtue of computer programs running on the respective computers and having a client-server relationship to each other.

The methods described herein (and the associated computer systems, apparatus and kits) can be performed mutatis mutandis with a detectable agent that binds non-phosphorylated cofilin and a detectable agent that binds phosphorylated cofilin, with the colocalization intensity, or the ratio of phosphorylated cofilin:total phosphorylated and non-phosphorylated cofilin being calculated from the amount of bound detectable agent that binds phosphorylated cofilin/(the amount of bound detectable agent that binds phosphorylated cofilin+the amount of bound detectable agent that binds non-phosphorylated cofilin).

As used herein the "subject" is a mammal. Preferably, the subject is a human. The subject may have a tumor diagnosed as malignant or a tumor not diagnosed as malignant.

All combinations of the various elements described herein are within the scope of the invention unless otherwise indicated herein or otherwise clearly contradicted by context.

This invention will be better understood from the Experimental Details, which follow. However, one skilled in the art will readily appreciate that the specific methods and results discussed are merely illustrative of the invention as described more fully in the claims that follow thereafter.

Experimental Details

Introduction

The activity status of cofilin is directly related to invasion, intravasation and metastasis of mammary tumors (12), but the overall activity of the cofilin pathway, and not just that of any single gene in the pathway, has been proposed to determine the invasiveness and metastatic phenotype of tumor cells (13). Recently, cofilin regulation has been modeled in invasive tumor cells (14). However, cofilin as a predictor of metastasis has not been resolved.

Materials and Methods

Paraffin-embedded human breast cancer tissue was arranged in TMA blocks (110 cores per block) using a Beecher Microarrayer, sectioned in slices (3-5 μm thick) and mounted on charged glass slides. After de-waxing, an antigen-retrieval was performed on Paskal system (125° C., 22 psi maximum for 2 minutes at pH 6.0, citrate buffer). After blocking with 1% BSA in TBS solution, samples were first incubated with primary antibodies (anti-cofilin, AE774, 5.6 μg/ml; anti-pS3-cofilin, AE441, 1.75 μg/ml) for one hour at RT then washed and incubated with secondary antibodies (donkey anti-chicken-Cy3, 5 μg/ml, and donkey anti-rabbit-Cy2, 10 μg/ml) for one hour at RT. All slides were washed and covered with glass using Mowiol mounting media with addition of DABCO anti-fading agent. Image acquisition was performed using a 20×objective (S-Fluor, NA0.75, Nikon) and a Lumen 200 (10% output, Prior, UK) light source.

For colocalization intensity analysis, the background area which corresponds to the pixels with low overlap distribution (ri<1.0) (15) was masked out. The highly colocalized areas between Cy2 and Cy3 were then found by masking out the pixels with low Pearson distribution (pi<1.0) (16). Finally, the colocalization intensity image ($I_F$) of the remaining highly colocalized pixels is built and its average value calculated. In the following, the Cy2 and Cy3 fluorescence channel intensities are respectively written $I_{Cy2}$ and $I_{Cy3}$ for each pixel forming
an image. The overlap coefficient R is conventionally calculated by averaging the overlap distribution $$R = \frac{1}{N_{Pixels}} \sum_{i=1}^{N_{Pixels}} r_i \text{ with } r_i = N_{Pixels} \times \frac{I_{F_i}}{\sqrt{\sum_{n=1}^{N_{Pixels}} I_{Cy2_n}^2 \times \sum_{n=1}^{N_{Pixels}} I_{Cy3_n}^2}}$$

where the colocalization intensity IF is given by the product of the local fluorescence intensity
in each channel: $I_F = I_{Cy2} \times I_{Cy3}$. Similarly, the Pearson coefficient P is calculated by averaging the Pearson distribution Pi:

$$P = \frac{1}{N_{Pixels}} \sum_{i=1}^{N_{Pixels}} p_i \text{ with}$$

$$p_i = N_{Pixels} \times \frac{(I_{Cy2_i} - I_{Cy2_{Average}}) \times (I_{Cy3_i} - I_{Cy3_{Average}})}{\sqrt{\sum_{n=1}^{N_{Pixels}} (I_{Cy2_n} - I_{Cy2_{Average}})^2 \times \sum_{n=1}^{N_{Pixels}} (I_{Cy3_n} - I_{Cy3_{Average}})^2}}$$

Experimental Results

It is disclosed herein that increased levels of cofilin expression and phosphorylated cofilin, when co-localized in tumor cells, predicts metastatic recurrence in breast cancer patients. A two antibody immunofluorescence staining approach has been applied to measure the intensity of this co-localization. It was found that the intensity is inversely correlated with time to metastasis (see FIG. 1). A significant increase in the risk of recurrence due to distal metastasis is observed with higher levels of phosphorylated cofilin present in tumors. FIG. 1(A) shows representative images of infiltrating ductal carcinoma stained with anti-phospho-Ser 3-cofilin and anti-pan-cofilin antibodies. Co-localization analysis was performed on 69 patients (30 patients from a 1980's cohort and 39 patients from a 1990's cohort). A high phosphorylated cofilin:total cofilin ratio (or high phosphorylated cofilin:total cofilin colocalization intensity) indicates an increased likelihood of recurrence due to distal metastasis.

Figure 1B:
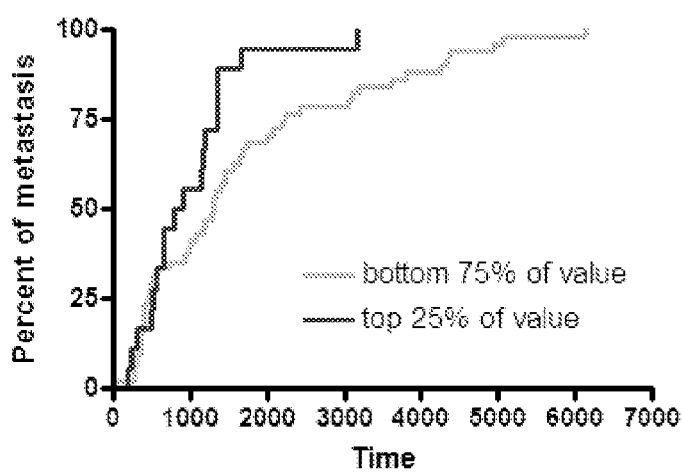
Figure 2:
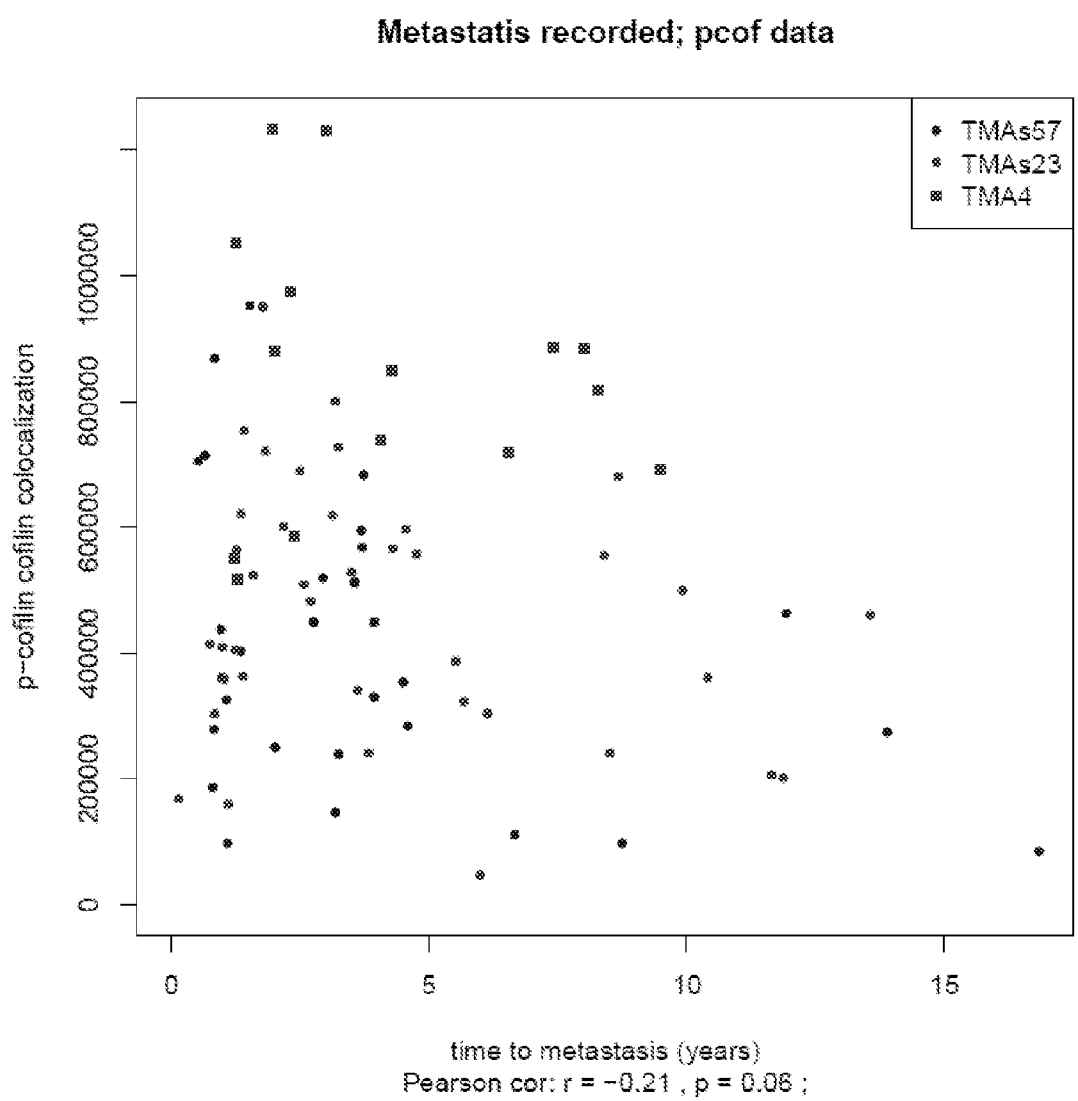
FIG. 2. Plot of raw data showing the inverse correlation between Phosphocofilin:total cofilin colocalization intensity and time to relapse due to distal metastasis in the same patient cohort shown in the Kaplan Meier analysis FIG. 1. (See Pearson Coefficient).

FIG. 2 is a plot of raw data showing the inverse correlation between phosphocofilin:total cofilin colocalization intensity and time to relapse due to distal metastasis in the same patient cohort shown in the Kaplan Meier analysis FIG. 1.

Figure 3:
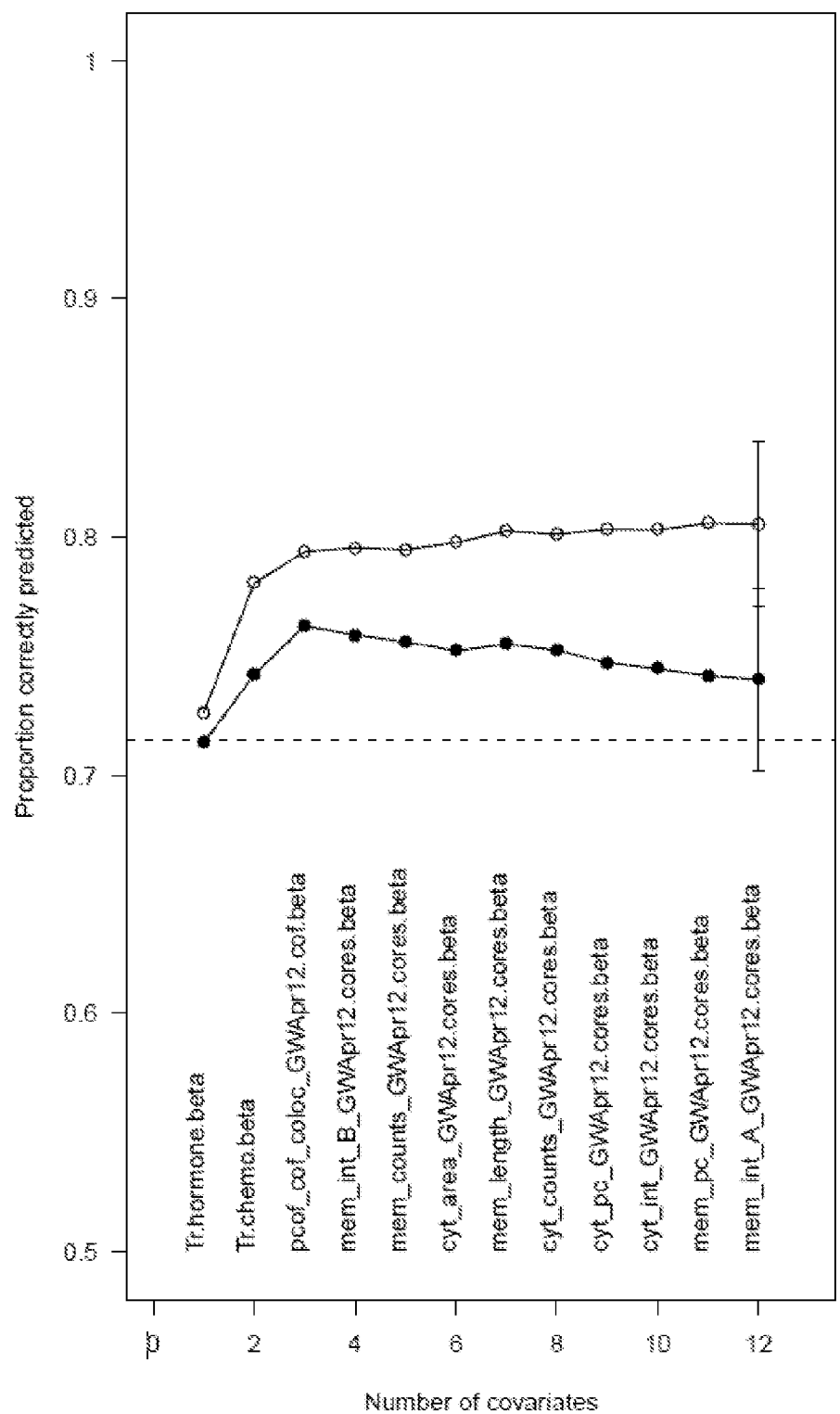
FIG. 3. Plot of proportion of correct predicts versus number of covariates.

FIG. 3 contains additional data showing the significance of pcofilin:cofilin colocalisation intensity in a multivariate model that incorporates other clinicopathological and image parameters. These are derived from imaging the further samples (from Guy's Hospital, London, n=141) within the Molecular Taxonomy of Breast Cancer International Consortium (METABRIC) cohort that recently uncovered further heterogeneous breast cancer subgroups with distinct clinical outcomes through analysis of paired DNA-RNA profiles on 1,992 tumors (Curtis, 2012). Pcofilin:cofilin colocalisation intensity was the most biologically significant image parameter measured among the others after adjustment for antiestrogen (hormonal; Tr.hormone.beta in the FIG. 3) and chemotherapy (Tr.chemo.beta in FIG. 3) effects.

This additional multivariate analysis takes into account the Reporting Recommendations for Tumor Marker Prognostic Studies (REMARK) guidelines, which assert that multivariate analysis is preferred over the log-rank assessment performed on the Kaplan-Meier data (see earlier analysis). (McShane 2005)

REFERENCES

1. Perou, C. M., et al. Molecular portraits of human breast tumours. *Nature* 406, 747-752 (2000).
2. Sorlie, T., et al. Gene expression patterns of breast carcinomas distinguish tumor subclasses with clinical implications. *Proc. Natl. Acad. Sci. U S. A.* 98, 10869-10874 (2001).
3. van de Vijver, M. J., et al. A gene-expression signature as a predictor of survival in breast cancer. *N Engl. J. Med.* 347, 1999-2009 (2002).
4. van't Veer, L. J., et al. Gene expression profiling predicts clinical outcome of breast cancer. *Nature* 415, 530-536 (2002).
5. Sorlie, T., et al. Repeated observation of breast tumor subtypes in independent gene expression data sets. *Proc. Natl. Acad. Sci. U S. A.* 100, 8418-8423 (2003).
6. Wang, Y., et al. Gene-expression profiles to predict distant metastasis of lymph-node-negative primary breast cancer. *Lancet* 365, 671-679 (2005).

7. Chang, H. Y., et al. Gene expression signature of fibroblast serum response predicts human cancer progression: similarities between tumors and wounds. *PLoS Biol* 2, E7 (2004).
8. Nguyen, D. X., Bos, P. D. & Massague, J. Metastasis: from dissemination to organ-specific colonization. *Nat Rev Cancer* 9, 274-284 (2009).
9. Kang, Y., et al. A multigenic program mediating breast cancer metastasis to bone. *Cancer Cell* 3, 537-549 (2003).
10. Minn, A. J., et al. Genes that mediate breast cancer metastasis to lung. *Nature* 436, 518-524 (2005).
11. Bos, P. D., et al. Genes that mediate breast cancer metastasis to the brain. *Nature* 459, 1005-1009 (2009).
12. Wang et al., *JCB*, 173(3):395-404 (2008).
13. Wang et al., *Nature* 7:429-440 (2007).
14. Tani et al., *Biophysical Journal,* 100(8) pp. 1883-1892 (2011).
15. Manders E M M, Verbeek F J, Aten J A. Measurement of co-localization of objects in dual colour confocal images J Microsc 1993; 169:375-382.
16. Gonzalez R C, Wintz P. Digital Image Processing. 2nd ed. Reading, Mass. Addison-Wesley; 1987.
17. McShane L M, Altman D G, Sauerbrei W, et al: Reporting recommendations for tumor marker prognostic studies (REMARK). *J Natl Cancer Inst* 97: 1180-1184, 2005
18. Curtis, C. et al. The genomic and transcriptomic architecture of 2,000 breast tumors reveals novel subgroups. *Nature* 486, 346-52 (2012)

What is claimed is:

1. A method of treating a subject having a tumor comprising:
   (A) identifying or having identified a subject as in need of an anti-metastatic treatment of a tumor, wherein the subject is identified as such by determining if an amount of phosphorylated cofilin bound: total amount of phosphorylated cofilin and non-phosphorylated cofilin bound colocalized in a sample of the tumor is in excess of a predetermined ratio value and indicative of metastasis, or a colocalization intensity value (IF) of an image of a sample obtained on the fluorescence imaging device within a colocalized area in the tumor is in excess of a predetermined IF value and indicative of metastasis, where a sample of the tumor has been contacted with (a) a fluorescent moiety-labeled agent that binds phosphorylated cofilin and (b) a fluorescent moiety-labeled agent which binds both phosphorylated cofilin and non-phosphorylated cofilin, and the method quantifies
   (i) the phosphorylated cofilin bound by (a) and
   (ii) the total of phosphorylated cofilin and non-phosphorylated cofilin bound by (b), and wherein the IF is the product of the intensity of fluorescence of the fluorescent moiety-labeled agent that binds phosphorylated cofilin and the fluorescence of the fluorescent moiety-labeled agent that binds both phosphorylated cofilin and non-phosphorylated cofilin at each pixel of the colocalized area,
   wherein the fluorescent moiety-labeled agent that binds phosphorylated cofilin comprises an antibody, or antigen-binding fragment thereof, that specifically binds phosphorylated cofilin, and wherein the fluorescent moiety-labeled agent which binds to phosphorylated cofilin and to non-phosphorylated cofilin comprises an antibody, or antigen-binding fragment thereof, which binds phosphorylated cofilin and which also binds non-phosphorylated cofilin, and
   (B) administering, to a subject so-identified in (A), an anti-metastatic therapy;
   wherein the tumor is a breast tumor.

2. The method of claim 1, wherein IF is intensity of (a) in pixels of an image of the sample multiplied by intensity of (b) in pixels of the image of the sample, optionally first masking out pixels with low Pearson distribution.

3. The method of claim 1, wherein the anti-metastatic therapy comprises trastuzumab and/or bevacizumab.

4. The method of claim 1, wherein the sample is a biopsy sample.

5. The method of claim 1, wherein the sample has been surgically removed from a subject.

6. The method of claim 1, wherein both the detectable agents each comprise a fluorescent moiety and wherein the detectable agent that binds to phosphocofilin comprises a different fluorescent moiety from the fluorescent moiety of the detectable agent that binds to phosphorylated cofilin and to non-phosphorylated cofilin.

7. The method of claim 1, wherein the phosphorylated cofilin and non-phosphorylated cofilin are human cofilin.

8. The method of claim 1, wherein the cofilin comprises SEQ ID NO:1.

9. The method of claim 1, wherein the sample is a paraffin-embedded biopsy sample.

10. The method of claim 1, wherein the fluorescent moiety-labeled agent which binds to phosphorylated cofilin and wherein the fluorescent moiety-labeled agent which binds to non-phosphorylated cofilin comprises an anti-pan-cofilin antibody.

11. The method of claim 1, wherein the fluorescent moiety-labeled agent which specifically binds to phosphorylated cofilin comprises an anti-phospho-Ser-3-cofilin antibody.

12. The method of claim 1, wherein the predetermined IF value-is determined from one or more subjects with malignant tumors which have not metastasized.

13. The method of claim 1, wherein the system performs the method for determining if the colocalization intensity value (IF) of an image of a sample obtained on the fluorescence imaging device within a colocalized area in the tumor is in excess of a predetermined IF value and indicative of metastasis.

* * * * *